United States Patent [19]

Holtkamp

[11] Patent Number: Plant 5,708

[45] Date of Patent: Apr. 1, 1986

[54] AFRICAN VIOLET PLANT NAMED COLUMBUS

[75] Inventor: Reinhold Holtkamp, Isselburg, Fed. Rep. of Germany

[73] Assignee: Gessellschaftsvertrag uber die Ergindergemeinschaft "OPTIMARA", Fed. Rep. of Germany

[21] Appl. No.: 568,450

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet plant named Columbus, characterized by its vigorous growth habit, girl type leaves, white-purple single flowers which occasionally have additional flower petals in the center of the flower, strong and upright stems, each of which carry 9 or more flowers, which are long lasting and non-dropping.

1 Drawing Figure

The present invention comprises a new and distinct cultivar of African violet plant, botanically known as *Saintpaulia ionantha,* and named Columbus.

The new cultivar was referred to during the breeding and selection process by the designation G 21/V, and is a product of a planned breeding program.

The new cultivar was originated from a cross made in a controlled breeding program in Isselburg, West Germany. The female, or seed parent was a cultivar designated 79 bl. girl. The male, or pollen parent was a cultivar designated X 89 bl. white frilled.

The new cultivar Columbus was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Columbus has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Columbus, which in combination distinguish this African violet as a new and distinct cultivar:

1. Columbus has girl type leaves, that is, leaves which are generally cupped and have a relatively bright green center at the bottom of the cup, surrounded by darker green foliage color.
2. Vigorous growth habit.
3. Two-toned white-purple single flowers, with occasionally additional flower petals.
4. Flowers are carried on strong upright stems which number 9 or more thereby providing a very floriferous cultivar.
5. The flowers are long lasting and non-dropping.

6. Plants can be grown relatively close together without stretching leaf petioles.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions approximately mid-day in November at Nashville, Tenn.

Botanical classification: *Saintpaulia ionantha,* Ramat. cv Columbus.

Parentage:

*Male parent.*—X 89 bl. white frilled.

*Female parent.*—79 bl. girl.

Propagation: The new cultivar holds its distinguishing characteristics through successive propagations by leaf cuttings and by division of shoots.

Plant: From 7 cm. to 9 cm. tall when grown in pots, approximately 18–20 cm. in diameter when fully grown.

*Leaves.*—General form: Round to heart shape. Diameter: 55–65 mm. Texture: Leather-like. Aspect: Velvety, slightly hairy, leaf center is bright green. Veins: Pronounced, light green and shiny. Color (upperside): Yellow green 147A. Color (underside): Yellow green 147D. Petiole: Light green, hairy.

*Flowers.*—Buds: Ball shape. Sepals: Medium green. Color: Light purple. Calyx: Flat funnel shape. Aspect: Short spear shape. Peduncle: Strong upright brownish/hairy green.

*Individual flowers.*—Size: 30–35 mm. Color: White-purple, two-tone. Upperside: Violet Group 88 between A-B; white. Underside: Violet Group 85D. When the new cultivar is grown under cooler conditions, the flower color will be more intensive, with higher temperatures causing the flower color to slightly fade. Borne: On sturdy upright stems, each of which carries 7–9 flowers. Shape: Typical violet shape; 2 small, 3 larger petals; additional flower petals occasionally present. Flowering time: 10–16 weeks after potting.

*Reproductive organs.*—Anthers: Two composed of four (4) anther cells; seed capsules pushed slightly through. Styles: Deep purple with white tips; ovary light green.

*Roots.*—White when young and active, brownish when older.

*Disease resistance.*—Goods as experienced to date.

General obervations: Columbus is a compact growing cultivar with girl type leaves and two-tone white-purple flowers. There are 7–9 or more upright flower stems each of which carry 7–9 or more single flowers, with additional flower petals occasionally appearing in the center of the flower. The flowers are long lasting and do not drop.

I claim:

1. A new and distinct cultivar of African violet plant named Columbus, as described and illustrated, and particularly characterized by its vigorous growth habit, girl type leaves, white-purple single flowers which occasionally have additional flower petals in the center of the flower, strong and upright stems, each of which carry 9 or more flowers, which are long lasting and non-dropping.

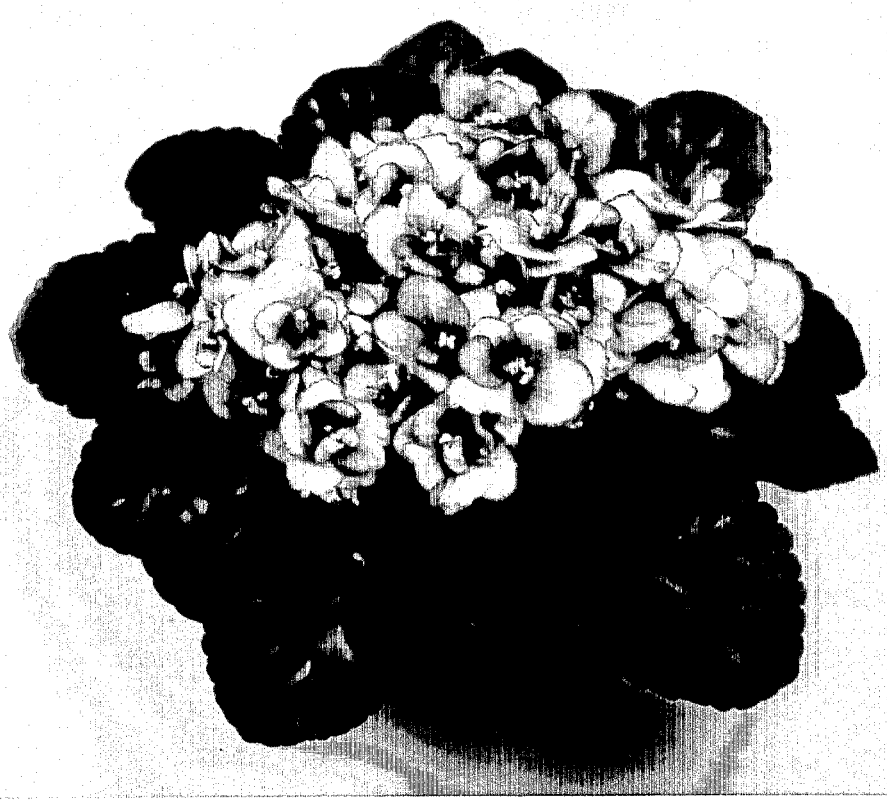

* * * * *